United States Patent [19]
Weigand

[11] Patent Number: 5,227,131
[45] Date of Patent: Jul. 13, 1993

[54] METAL ALLOY FOR CAST PROSTHETIC FRAMES IN DENTISTRY

[75] Inventor: Hans-Hermann Weigand, Tonisvorst, Fed. Rep. of Germany

[73] Assignee: Thyssen Stahl Aktiengesellschaft, Fed. Rep. of Germany

[21] Appl. No.: 757,518

[22] Filed: Sep. 11, 1991

[30] Foreign Application Priority Data

Sep. 12, 1990 [DE] Fed. Rep. of Germany ....... 4028870

[51] Int. Cl.$^5$ ...................... C22C 19/07; C22C 30/00
[52] U.S. Cl. .................... 420/436; 420/588; 433/207
[58] Field of Search ............. 420/436, 588; 433/207; 148/408, 419, 425, 442

[56] References Cited

U.S. PATENT DOCUMENTS

| | | | |
|---|---|---|---|
| 2,750,283 | 6/1956 | Loveless | 420/586 |
| 4,116,724 | 9/1978 | Hirschfeld et al. | 148/425 |
| 4,728,495 | 3/1988 | Rademacher | 420/436 |
| 5,039,574 | 8/1991 | Kulmburg | 420/436 |

FOREIGN PATENT DOCUMENTS

| | | |
|---|---|---|
| 642040 | 2/1937 | Fed. Rep. of Germany. |
| 2225577 | 12/1973 | Fed. Rep. of Germany. |
| 3744491 | 3/1989 | Fed. Rep. of Germany. |
| 3941820 | 6/1991 | Fed. Rep. of Germany. |
| 61-003860 | 1/1986 | Japan. |

Primary Examiner—R. Dean
Assistant Examiner—Margery S. Phipps
Attorney, Agent, or Firm—Cushman, Darby & Cushman

[57] ABSTRACT

A metal alloy for cast prosthetic frames in dentistry, consisting of (in % by weight)

| | |
|---|---|
| 0.1 to 0.3 | % C |
| up to 1.5 | % Si |
| up to 3 | % Mn |
| 25 to 35 | % Cr |
| 3 to 6.5 | % Mo |
| 0.5 to 5 | % Ta |
| 0.15 to 0.40 | % N | remainder cobalt and residual impurities.

4 Claims, No Drawings

METAL ALLOY FOR CAST PROSTHETIC FRAMES IN DENTISTRY

The present invention relates to a metal alloy based on cobalt for cast prosthetic structures useful in dentistry.

BACKGROUND OF THE INVENTION

In the past, primarily carbon-containing cobalt-chrome-molybdenum alloys, also called model casting alloys, have been used for the manufacture of prosthetic structures for removable dental prostheses. Known alloys of this type contain 0.3 to 0.6 % carbon, up to 1% each silicon and manganese, 27 to 32% chromium, 3 to 8% molybdenum, remainder cobalt with the unavoidable impurities occasioned by the manufacture ("Das Dental Vademecum", a list of dental and dental-technology working means and materials, editor: Federal Board of Doctors (Federal Association of German Dentists, BDZ), edition 1989/90). The molybdenum content of these alloys can be replaced entirely or partially by tungsten according to DIN 13912, part 2 (outline). However, tungsten is only approximately half as effective as molybdenum in its effect on corrosion resistance. These alloys generally exhibit satisfactory mechanical and corrosion-chemical properties for the purpose intended. However, their relatively low deformability, with values for the elongation at rupture ($A_5$) between 2 and 6%, permits only slight plastic deformations without the danger of rupture.

In order to improve the deformability which is necessary e.g. in aligning work on the holding clamps of prosthetic frames, titanium-containing alloys and other materials have been suggested in which a part of the carbon was replaced by nitrogen (see Published German Patent Application DE 22 25 557 C2). These alloys exhibit relatively high values for the 0.2% permanent elongation limit (around 650 N/mm$^2$) and elongations at rupture up to 12%. It would be very desirable to raise the 0.2% permanent elongation limit of these alloys to values above 670 N/mm$^2$ for the manufacture of lighter and more graceful prosthetic frames, by means of the addition of nitrogen. However, this is not possible because the solubility limit with nitrogen contents above 0.3%. This renders the manufacture of pore-free cast objects impossible.

SUMMARY OF THE INVENTION

The object of the present invention is to provide a corrosion-resistant alloy which can be readily cast under the conditions of a dental laboratory, which has sufficiently high rupture deformation values (elongation at rupture $A_5 \geq 8\%$) and which has high mechanical stability under load (0.2% permanent elongation limit above 670 N/mm$^2$). These and other objects are achieved by means of a metal alloy having the following composition in % by weight:

| | |
|---|---|
| 0.1 to 0.3 | % C |
| up to 1.5 | % Si |
| up to 3 | % Mn |
| 25 to 35 | % Cr |
| 3 to 6.5 | % Mo |
| 0.5 to 5 | % Ta |
| 0.15 to 0.40 | % N | remainder cobalt including impurities occasioned by melting.

It is preferable if the molybdenum content exceeds the tantalum content and their total content (% Mo)+(% Ta) is greater than or equal to 4.5%.

The cobalt alloy can also contain up to 0.5% boron, preferably 0.01 to 0.1 boron. Boron improves the fluidity and the viscosity of the alloy in this range.

It was surprisingly determined that an addition of tantalum results in a noticeable increase of the mechanical properties without the other required properties, such as corrosion resistance or workability, being adversely affected to any appreciable extent. This will be illustrated below in a few examples.

DETAILED DESCRIPTION OF PREFERRED EMBODIMENTS

EXAMPLE 1

The following Table 1 presents the mechanical properties determined in cast tensile [tensile strength] specimens.

TABLE 1

| Alloy No. | C % | Cr % | Mo % | Ta % | N % | Other | (1) | (2) | (3) | (4) |
|---|---|---|---|---|---|---|---|---|---|---|
| 1 | 0.2 | 29 | 4.93 | — | 0.26 | Si, B | 638 | 924 | 12.5 | 20.3 |
| 2 | 0.17 | 29.8 | 4.14 | — | 0.30 | Si, B | 665 | 947 | 11.7 | 17.7 |
| 3 | 0.21 | 29.2 | 3.1 | 1.07 | 0.23 | Si, B | 591 | 875 | 11.7 | 13.7 |
| 4 | 0.17 | 29.0 | 0.05 | 5.26 | 0.29 | Si, B | 488 | 799 | 8.8 | 10.0 |
| 5 | 0.19 | 29.0 | 2.94 | 1.92 | 0.21 | Si, B | 686 | 1057 | 13.2 | 16.0 |
| 6 | 0.21 | 18.6 | 4.94 | 2.08 | 0.27 | Si, B | 718 | 1015 | 8.0 | 11.0 |

(1) 0.2 limit $R_{p0.2}$ N/mm$^2$
(2) Tensile Strength $R_m$ N/mm$^2$
(3) Elongation at break $A_5$ in %
(4) Reduction of area when breaking Z in %

Alloys 1 and 2 correspond to those in accordance with Published German Patent Application DE 22 25 577 C2.
Alloys 3 and 4 are reference alloys outside of the range for the present invention.
Alloys 5 and 6 have a composition in accordance with the invention.

Alloys 1 and 2, which are cited for comparison and which correspond in their composition to the claims of DE 22 25 577 C2, achieve relatively favorable values of strength and rupture deformation. However, as already mentioned, a further increase of the mechanical properties is not possible for this alloy base. The alloys with an addition of tantalum do not result in every instance in the desired improvements of properties, as demonstrated by the values of reference alloys 3 and 4, which are not in accordance with the invention. Only the coordination of the molybdenum and tantalum contents in accordance with the invention in alloys 5 and 6 yields noticeably favorable values for the 0.2% permanent elongation limit to above 60 N/mm$^2$ and elongation at rupture values of 8% and higher.

EXAMPLE 2

Current density - potential - curves were recorded in artificial saliva according to Fusayama with and without slot using known cobalt alloys and cobalt alloys in accordance with the invention in order to test corrosion resistance. The breakdown potential served as the criterion for the corrosion resistance and, in the case of the specimens with slot (plastic ring put on), the repassivation potential as well. The measured values are given in the following Table 2.

TABLE 2

| Alloy No. | C % | Cr % | Mo % | Ta % | N % | Other | (A) a) | (A) b) | (B) b) |
|---|---|---|---|---|---|---|---|---|---|
| 1 | 0.2 | 29 | 4.93 | — | 0.26 | Si, B | +780 | +780 | +550 |
| 7 | 0.2 | 28.6 | 4.97 | 1.50 | 0.26 | Si, B | +610 | +640 | +640 |

(A) Breakdown Potential in mV
(B) Repassivation potential in mV
1 - according to DE 2 225 577 C2
7 - in accordance with the invention
a) without slot
b) with slot It is apparent from the results in Table 2 that all cobalt alloys are to be considered as resistant to the environment in the mouth, as indicated by their breakdown potentials above +600 mV, since potentials of +300 mV at the most occur in the mouth. The repassivation potentials are at or above the breakdown potentials in the case of the alloy of the invention so that the alloys readily repassivate even under slot conditions, which underscores their suitability for use in the mouth.

What is claimed is:

1. A metal alloy for cast prosthetic frames in dentistry, consisting of (in % by weight)

| | |
|---|---|
| 0.1 to 0.3 | % C |
| up to 1.5 | % Si |
| up to 3 | % Mn |
| 25 to 35 | % Cr |
| 3 to 6.5 | % Mo |
| 0.5 to 5 | % Ta |
| 0.15 to 0.40 | % N |
| 0 to 0.5 | % B | remainder cobalt, and unavoidable impurities.

2. A metal alloy as set forth in claim 1 in which the molybdenum content exceeds the tantalum content and their total content (% Mo)+(% Ta) is at least equal to 4.5%.

3. A metal alloy for cast prosthetic frames in dentistry, consisting of (in % by weight)

| | |
|---|---|
| 0.1 to 0.3 | % C |
| up to 1.5 | % Si |
| up to 3 | % Mn |
| 25 to 35 | % Cr |
| 3 to 6.5 | % Mo |
| 0.5 to 5 | % Ta |
| 0.15 to 0.40 | % N |
| 0.01 to 0.1 | % B | remainder cobalt, and unavoidable impurities.

4. A metal alloy as set forth in claim 3 in which the molybdenum content exceeds the tantalum content and their total content (% Mo)+(% Ta) is at least equal to 4.5%.

* * * * *